US010143421B2

(12) United States Patent
Weast et al.

(10) Patent No.: US 10,143,421 B2
(45) Date of Patent: Dec. 4, 2018

(54) SYSTEM AND METHOD FOR USER NUDGING VIA WEARABLE DEVICES

(71) Applicant: INTEL CORPORATION, Santa Clara, CA (US)

(72) Inventors: John C. Weast, Portland, OR (US); Glen J. Anderson, Beaverton, OR (US); Giuseppe Raffa, Portland, OR (US)

(73) Assignee: INTEL CORPORATION, Santa Clara, CA (US)

( * ) Notice: Subject to any disclaimer, the term of this patent is extended or adjusted under 35 U.S.C. 154(b) by 0 days.

(21) Appl. No.: 14/666,618

(22) Filed: Mar. 24, 2015

(65) Prior Publication Data
US 2016/0284172 A1    Sep. 29, 2016

(51) Int. Cl.
*H04B 3/36* (2006.01)
*A61B 5/00* (2006.01)
*G08B 21/06* (2006.01)
*A61B 5/11* (2006.01)

(52) U.S. Cl.
CPC ............ *A61B 5/6802* (2013.01); *A61B 5/486* (2013.01); *A61B 5/0022* (2013.01); *A61B 5/1112* (2013.01); *A61B 5/1116* (2013.01); *A61B 5/1118* (2013.01); *G08B 21/06* (2013.01)

(58) Field of Classification Search
None
See application file for complete search history.

(56) References Cited

U.S. PATENT DOCUMENTS

| 2012/0136231 | A1* | 5/2012 | Markel | A61B 5/0015 |
| | | | | 600/388 |
| 2014/0232534 | A1* | 8/2014 | Birnbaum | G06F 3/016 |
| | | | | 340/407.1 |

* cited by examiner

*Primary Examiner* — Adolf Dsouza
(74) *Attorney, Agent, or Firm* — Womble Bond Dickinson (US) LLP (57) ABSTRACT

A method is described to facilitate behavioral nudging. The method includes receiving sensory data from one or more wearable devices, determining a context for a user wearing the one or more wearable devices based on the sensory data, determining a mechanism to nudge the user to reinforce user behavior based on stored preferences and policies and transmitting a nudging stimulus to at least one of the wearable devices via the determined mechanism to provide a notification to the user.

19 Claims, 5 Drawing Sheets

SYSTEM AND METHOD FOR USER NUDGING VIA WEARABLE DEVICES

FIELD

Embodiments described herein generally relate to wearable computing. More particularly, embodiments relate to nudging based wearable devices.

BACKGROUND

Modern clothing and other wearable accessories may incorporate computing or other advanced electronic technologies. Such computing and/or advanced electronic technologies may be incorporated for various functional reasons or may be incorporated for purely aesthetic reasons. Such clothing and other wearable accessories are generally referred to as "wearable technology" or "wearable computing devices."

Wearable devices are becoming prevalent for enabling users to accomplish various tasks while on the go. For instance, health and fitness, tracking and simple phone-like applications are becoming pervasive. Currently, wearable devices that provide notification (or nudging) based feedback are available. For example, a posture device is available that includes a sensor to detect whether a user is sitting with proper posture. Such a device may vibrate in order to notify the user upon detecting improper posture. However, these devices are limited since they only perform specific applications.

BRIEF DESCRIPTION OF THE DRAWINGS

Embodiments are illustrated by way of example, and not by way of limitation, in the figures of the accompanying drawings in which like reference numerals refer to similar elements.

DETAILED DESCRIPTION

Embodiments may be embodied in systems, apparatuses, and methods for enhanced awareness, as described below. In the description, numerous specific details, such as component and system configurations, may be set forth in order to provide a more thorough understanding of the present invention. In other instances, well-known structures, circuits, and the like have not been shown in detail, to avoid unnecessarily obscuring the present invention.

Embodiments provide for a behavioral nudging mechanism to leverage a multitude of user wearable devices in order to provide contextual and in the flow non-interruptive notifications/nudges for positive reinforcement of behavior. In such embodiments, nudges may be configured by the user based on behaviors and/or actions that are to be tracked. In further embodiments, ways in which nudges are discreetly perceived by the user (e.g., haptic, audio, light, etc.) may also be configured.

According to one embodiment, data signals received from the wearable devices (e.g., wrist worn devices, head worn devices, censored clothing, shoes, socks, belts, etc.) are combined to gain advanced insight. In a further embodiment, the same wearable devices are equipped with actuation systems to provide recommendations for positive (or negative) behavior reinforcement by leveraging discreet nudging. For example, a user wearing a wrist worn wearable device and a back posture and activity coach wearable device in the presence of friends may be nudged upon the user commencing chewing of fingernails, as detected by the wrist worn device. In one embodiment the nudging is delivered via the back posture and activity coach wearable device even though that device is not aware of the fingernail chewing detection.

In other embodiments, the behavioral nudging mechanism may implement context and/or setting information to become informed and modified through new user preferences or by changes in community wide settings (e.g., encourage recycling).

Figure 1:
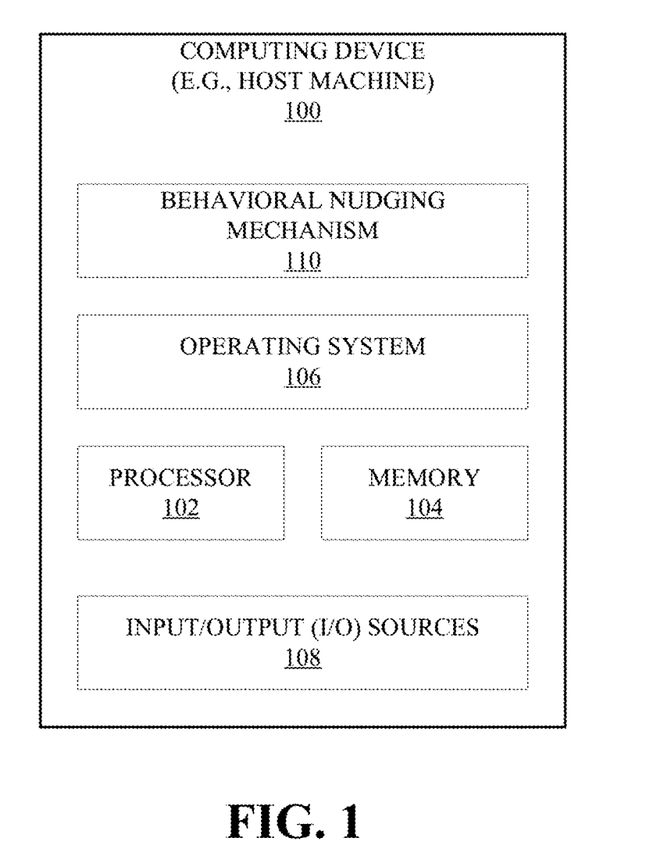
FIG. 1 illustrates a behavioral nudging mechanism at a computing device according to one embodiment.

FIG. 1 illustrates one embodiment of a behavioral nudging mechanism 110 at a computing device 100. In one embodiment, computing device 100 serves as a host machine for hosting behavioral nudging mechanism ("nudging mechanism") 110 that includes a combination of any number and type of components for detecting stimuli and nudging at computing devices, such as computing device 100. In one embodiment, computing device 100 includes a wearable device. Thus, implementation of nudging mechanism 110 results in computing device 100 being an assistive device to provide recommendations to a wearer of computing device 100.

In other embodiments, behavioral nudging operations may be performed at a computing device 100 including large computing systems, such as mobile computing devices, such as cellular phones including smartphones (e.g., iPhone® by Apple®, BlackBerry® by Research in Motion®, etc.), personal digital assistants (PDAs), tablet computers (e.g., iPad® by Apple®, Galaxy 3® by Samsung®, etc.), laptop computers (e.g., notebook, netbook, Ultrabook™, etc.), e-readers (e.g., Kindle® by Amazon®, Nook® by Barnes and Nobles®, etc.), etc. In yet other embodiments, computing device 100 may include server computers, desktop computers, etc., and may further include set-top boxes (e.g., Internet-based cable television set-top boxes, etc.), global positioning system (GPS)-based devices, etc.

Computing device 100 may include an operating system (OS) 106 serving as an interface between hardware and/or physical resources of the computer device 100 and a user. Computing device 100 further includes one or more processors 102, memory devices 104, network devices, drivers, or the like, as well as input/output (I/O) sources 108, such as touchscreens, touch panels, touch pads, virtual or regular keyboards, virtual or regular mice, etc.

Figure 2:
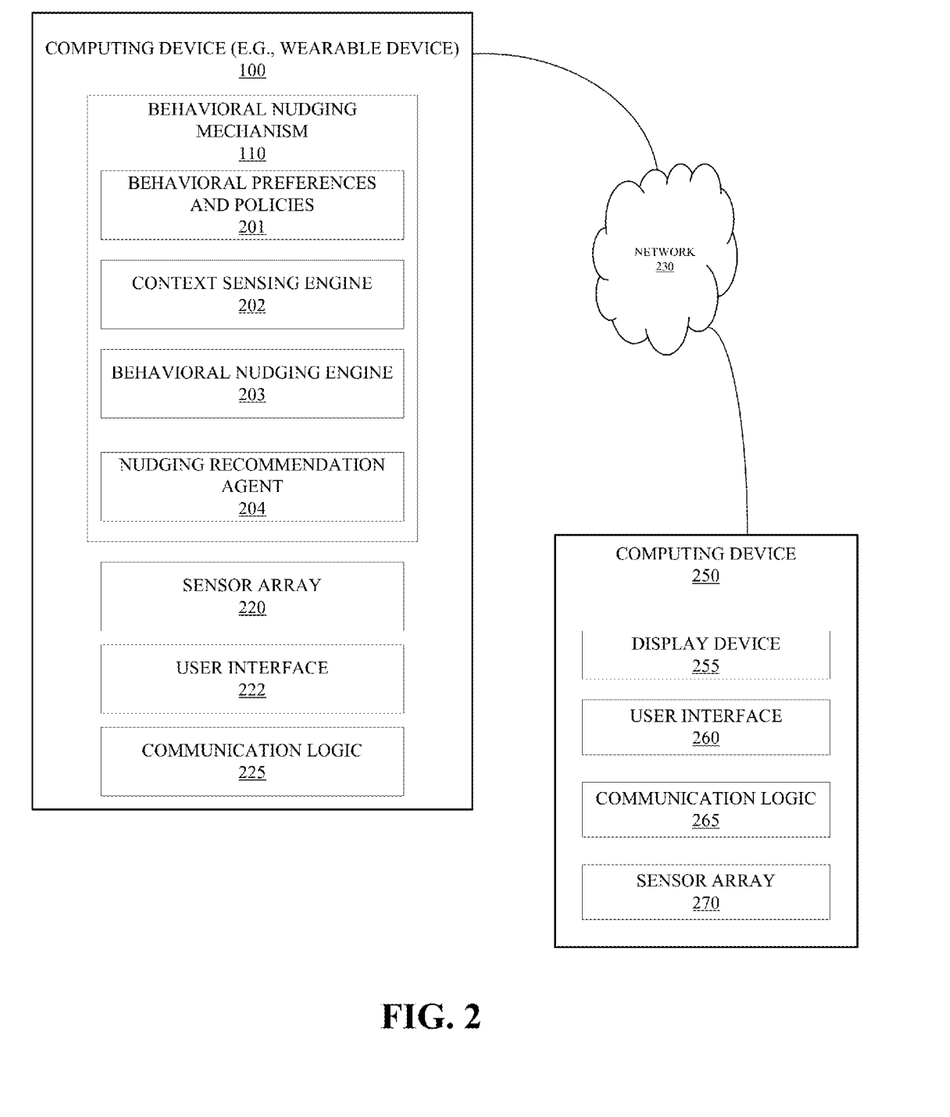
FIG. 2 illustrates one embodiment of a behavioral nudging mechanism.

FIG. 2 illustrates a behavioral nudging mechanism 110 employed at computing device 100. In one embodiment, behavioral nudging mechanism 110 may include any number and type of components, such as: behavioral preferences and policies module 201, context sensing engine 202, behavioral nudging engine 203 and nudging recommendation agent 204. In one embodiment, behavioral preferences and policies module 201 stores preset behavioral (or other) preferences and policies. In such an embodiment, the preferences and policies may be provided by the user or entities other than a device user (e.g., a doctor, local neighborhood community, etc.).

In other embodiments, behavioral preferences and policies module 201 keeps track of user responses to nudging Implicitly, in such embodiments, behavior is tracked after nudging is performed in order to determine whether the nudging was recognized, and whether the advice was followed by the user. Accordingly, behavioral preferences and policies module 201 collects data to improve the nudging mechanism in terms of timing (e.g., when the nudging should occur to have the best results) and actuation (e.g. user recognizes light more than audio, or vice versa).

In yet another embodiment, behavioral preferences and policies module 201 may learn from others. For example, behavioral preferences and policies module 201 may monitor types of nudges used to persuade other users in related contexts and with related profiles. Such information may be used as part of a determination as to the best approach with a given individual in a certain situation. In further embodiments, behavioral preferences and policies module 201 may also test different modalities and intensity to perform self-tuning.

In such embodiments, behavioral preferences and policies module 201 monitors a success level of a feedback instance to the user in order to learn which level and type of feedback is best for that user. For example, if behavioral preferences and policies module 201 provides for both light and medium vibration amplitudes to be used to signal the user to sit straight, and the user only responds to the medium, behavioral preferences and policies module 201 would no longer use the light vibration and only use the medium.

In other embodiments, behavioral preferences and policies module 201 may implement collaborative filtering algorithms for recommendation engines to determine various user likes or dislikes. In such embodiments, behavioral preferences and policies module 201 may consider user demographic, location, and/or time in determining a type of nudging stimulus to implement. For example, behavioral preferences and policies module 201 may determine that all people in their twenties in a particular location, a particular time of day, day of week, etc. likes a particular type of feedback. Such an implementation may occur dynamically such that decisions may change overtime depending on user context.

Figure 3:
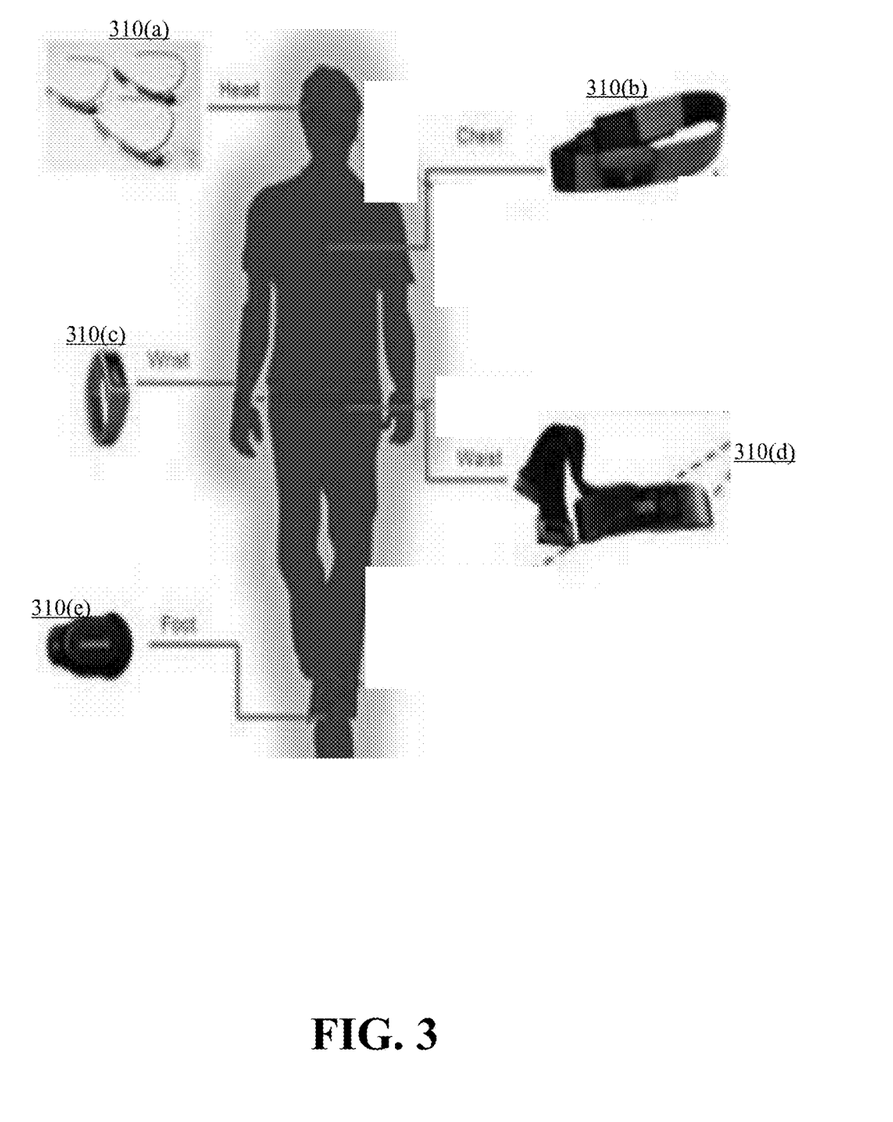
FIG. 3 illustrates one embodiment of wearable devices implemented by a behavioral nudging mechanism.

Context sensing engine 202 receives data from wearable devices to determine user context (e.g., a current location of a user, one or more persons accompanying the user, devices being worn by the user, etc.). The data may include raw or analyzed data. For instance, data may include heart rate, steps taken, real time video (such as from a head worn wearable device), etc. FIG. 3 illustrates one embodiment of wearable devices from which context sensing engine 202 may receive data. As shown in FIG. 3, devices 310(*a*)-310(*e*) may be worn on a user's head, chest, wrist, waist and foot, respectively. In such embodiments, data is transmitted from each device 310 to context sensing engine 202.

According to one embodiment, context sensing engine 202 is located at a wearable device 310. In such an embodiment, context sensing engine 202 may receive audio and image data from sensor array 220 (FIG. 2), where the image data may be in the form of a sequence of images or frames (e.g., video frames). Sensor array 220 may include an image capturing device, such as a camera. Such a device may include various components, such as (but are not limited to) an optics assembly, an image sensor, an image/video encoder, etc., that may be implemented in any combination of hardware and/or software. The optics assembly may include one or more optical devices (e.g., lenses, mirrors, etc.) to project an image within a field of view onto multiple sensor elements within the image sensor. In addition, the optics assembly may include one or more mechanisms to control the arrangement of these optical device(s). For example, such mechanisms may control focusing operations, aperture settings, exposure settings, zooming operations, shutter speed, effective focal length, etc. Embodiments, however, are not limited to these examples.

Image sources may further include one or more image sensors including an array of sensor elements where these elements may be complementary metal oxide semiconductor (CMOS) sensors, charge coupled devices (CCDs), or other suitable sensor element types. These elements may generate analog intensity signals (e.g., voltages), which correspond to light incident upon the sensor. In addition, the image sensor may also include analog-to-digital converter(s) ADC(s) that convert the analog intensity signals into digitally encoded intensity values. Embodiments, however, are not limited to these examples. For example, an image sensor converts light received through optics assembly into pixel values, where each of these pixel values represents a particular light intensity at the corresponding sensor element. Although these pixel values have been described as digital, they may alternatively be analog. As described above, the image sensing device may include an image/video encoder to encode and/or compress pixel values. Various techniques, standards, and/or formats (e.g., Moving Picture Experts Group (MPEG), Joint Photographic Expert Group (JPEG), etc.) may be employed for this encoding and/or compression.

In a further embodiment, sensor array 220 may include other types of sensing components, such as context-aware sensors (e.g., myoelectric sensors, temperature sensors, facial expression and feature measurement sensors working with one or more cameras, environment sensors (such as to sense background colors, lights, etc.), biometric sensors (such as to detect fingerprints, facial points or features, etc.), and the like.

According to one embodiment, computing device 100 (e.g., as implemented in a wearable device such as device 310(*a*)) may be in communication with computing device 250 (e.g., as implemented in another wearable device such as device 310(*b*)) over one or more networks, such as network 230 (e.g., Body Area Network (BAN), cloud network, the Internet, intranet, cellular network, proximity or near proximity networks, etc.). Computing device 250 may further include user interface 260, communication logic 265, and one or more software applications including nudging mechanism 110. However in other embodiments context sensing engine 202 may be implemented in a cloud computing application performed within network 230

According to one embodiment, context sensing engine 202 uses the contextual data as received from one or more sensors 220 to determine a nudging method and which wearable device that is to be used to perform the nudging. For instance, context sensing engine 202 may determine from wearable device data that a user is in a public space with friends whom the user does not want to be aware of a bad habit the user may have (e.g., lip biting, biting finger nails, etc.). In such an instance, context sensing engine 202 may select a nudging method that is discreet. However, context sensing engine 202 may determine that the user is jogging with friends as part of a shared weight loss regiment. In such an instance, context sensing engine 202 may select an audible or visible notification upon the user surpassing a key weight thresholds.

In one embodiment, context sensing engine 202 accesses behavioral preferences and policies module 201 to determine a course of action. In such an embodiment context sensing engine 202 determines a type of nudging to implement at a wearable device 310 that is needed at that moment to encourage the user to be in conformance with policies provided in behavioral preferences and policies module 201.

Behavioral nudging engine 203 transmits a signal to wearable device 310 indicating a nudging stimulus that is to be implemented. In one embodiment, the nudging does not need to be performed on the same device 310 as the device 310 that generated the data that encouraged the nudging. For example, data from chest (e.g., a heart rate monitor) could result in a visual indicator in the head worn device 310(a) and/or a vibration in the wrist worn device 310(c). According to one embodiment, a current activity and context of the user may change the manner in which behavioral nudging engine 203 transmits a nudge. For example, behavioral nudging engine 203 may maintain discretion in transmitting a nudge in instances where a user is a car or while dining with others in a restaurant, as opposed to transmitting an overt nudge in instances when a user is alone.

Nudging recommendation agent 204 supports the ability to monitor user behavior and responsive nudging across multiple users implementing nudging mechanism 110. In one embodiment, nudging recommendation agent 204 applies successful nudging approaches to other nudging mechanism 110 users that match particular profiles and context (e.g., weight-loss goals, interests, personality traits, job, current location, social circumstances, etc.). In such an embodiment, nudging recommendation agent 204 receives high-level goals from a user (e.g. lose 10 pounds) and works across various contexts and modalities to shape behavior based on previously successful nudging methods. Thus, nudging recommendation agent 204 may observe schedule and other contextual factors to nudge a multitude of user's behavior, in addition to encouraging more activity.

Moreover, nudging recommendation agent 204 may communicate with behavioral preferences and policies module 201 to apply acquired nudging approaches to the user of nudging mechanism 110. In one embodiment, nudging recommendation agent 204 may facilitate society wide (e.g., city, state, national, world, etc.) nudging. In such an embodiment, nudging recommendation agent 204 may encourage (e.g., recycling) or discourage (e.g., activities that spread diseases) user behavior in certain locations.

User interface 222 provides for user interaction with computing device 100. In one embodiment, user interface 222 enables a user to interact via gestures and/or audio commands in order to provide feedback to nudging mechanism 110. In such an embodiment, a user may dismiss or acknowledge a nudge with a gesture. In other embodiments, additional feedback mechanisms may be implemented.

Communication logic 225 may be used to facilitate dynamic communication and compatibility between various computing devices, such as computing device 100 and computing devices 250 (such as a mobile computing device, a desktop computer, a server computing device, etc.), storage devices, databases and/or data sources, such as database 240, networks, such as network 270 (e.g., cloud network, the Internet, intranet, cellular network, proximity networks, such as Bluetooth, Bluetooth low energy (BLE), Bluetooth Smart, Wi-Fi proximity, Radio Frequency Identification (RFID), Near Field Communication (NFC), Body Area Network (BAN), etc.), connectivity and location management techniques, software applications/websites, (e.g., social and/or business networking websites, such as Facebook®, LinkedIn®, Google+®, Twitter®, etc., business applications, games and other entertainment applications, etc.), programming languages, etc., while ensuring compatibility with changing technologies, parameters, protocols, standards, etc.

It is contemplated that any number and type of components 201-225 of nudging mechanism 110 may not necessarily be at a single computing device and may be allocated among or distributed between any number and type of computing devices, including computing devices 100, 250 having (but are not limited to) server computing devices, cameras, PDAs, mobile phones (e.g., smartphones, tablet computers, etc.), personal computing devices (e.g., desktop devices, laptop computers, etc.), smart televisions, servers, wearable devices, media players, any smart computing devices, and so forth. Further examples include microprocessors, graphics processors or engines, microcontrollers, application specific integrated circuits (ASICs), and so forth. Embodiments, however, are not limited to these examples.

Communication logic 265 of computing devices 250 may be similar to or the same as communication logic 225 of computing device 100 and may be used to facilitate communication nudging mechanism 110 at computing device 100 and one or more software applications at computing devices 250 over one or more networks, such as network 270. Further, logic 225 and 265 may be arranged or configured to use any one or more of communication technologies, such as wireless or wired communications and relevant protocols (e.g., Wi-Fi®, WiMAX, Ethernet, etc.), to facilitate communication over one or more networks, such as network 270 (e.g., Internet, intranet, cloud network, proximity network (e.g., Bluetooth, etc.).

Throughout this document, terms like "logic", "component", "module", "framework", "engine", "point", and the like, may be referenced interchangeably and include, by way of example, software, hardware, and/or any combination of software and hardware, such as firmware. Further, any use of a particular brand, word, term, phrase, name, and/or acronym, such as "avatar", "avatar scale factor", "scaling", "animation", "human face", "facial feature points", "zooming-in", "zooming-out", etc., should not be read to limit embodiments to software or devices that carry that label in products or in literature external to this document.

It is contemplated that any number and type of components may be added to and/or removed from nudging mechanism 110 to facilitate various embodiments including adding, removing, and/or enhancing certain features. For brevity, clarity, and ease of understanding of nudging mechanism 110, many of the standard and/or known components, such as those of a computing device, are not shown or discussed here. It is contemplated that embodiments, as described herein, are not limited to any particular technology, topology, system, architecture, and/or standard and are dynamic enough to adopt and adapt to any future changes.

Figure 4:
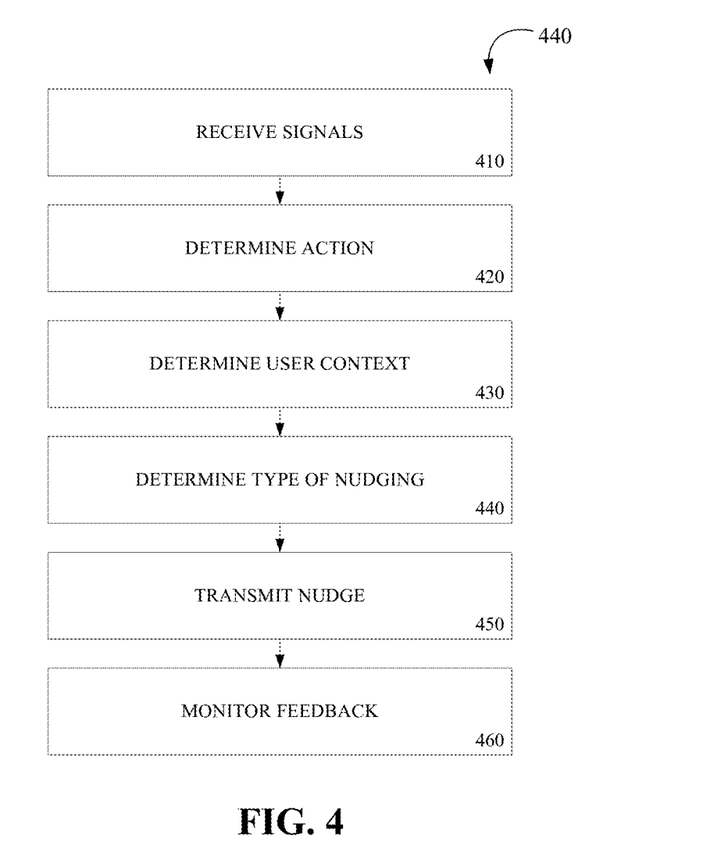
FIG. 4 is a flow diagram illustrating one embodiment of a process performed by a behavioral nudging mechanism.

FIG. 4 is a flow diagram illustrating one embodiment of a process 400 performed by a behavioral nudging mechanism. Process 400 may be performed by processing logic that may comprise hardware (e.g., circuitry, dedicated logic, programmable logic, etc.), software (such as instructions run on a processing device), or a combination thereof. In one embodiment, method 400 may be performed by behavioral nudging mechanism 110. The processes of method 400 are illustrated in linear sequences for brevity and clarity in presentation; however, it is contemplated that any number of them can be performed in parallel, asynchronously, or in different orders. For brevity, clarity, and ease of understanding, many of the details discussed with reference to FIGS. 1-3 are not discussed or repeated here.

At processing block 410, context sensing engine 202 receives sensory data from one or more wearable devices 310. At processing block 420, context sensing engine 202 communicates with behavioral preferences and policies module 201 to determine a course of action that is to be performed based on the received signals. At processing block 430, context sensing engine 202 determines user context based on received contextual data. At processing block 440, context sensing engine 202 determines a type, and location, of nudging to be performed based upon context and the determined course of action. At processing block 450, behavioral nudging engine 203 transmits a nudge to a specified wearable device 310. At processing block 460, behavioral preferences and policies module 201 monitors feedback via user interface 222 to track how the user responded to the nudge.

According to one embodiment, behavioral nudging mechanism 110 may perform nudging of users prior to an event, rather than after the detection of the event. For example, when a user's fingers approach the mouth in a configuration consistent with the biting of fingernails, behavioral nudging mechanism 110 may provide a nudge to avoid that behavior. Alternatively, behavioral nudging mechanism 110 may be used to encourage good behavior by nudging a user to walk towards a salad bar instead of a pizza bar. Further, behavioral nudging mechanism 110 may perform nudging of users after an event in order to not disturb the user (e.g., performing a strenuous or potentially dangerous activity such as free climbing), or for privacy reasons (e.g., people around and the user doesn't want to be nudged in public).

The above described behavioral nudging mechanism 110 may be implemented in various applications. For example nudging mechanism 110 may be used for health/fitness, grocery/health identification (ID), product compatibility, and car and safety applications. For health/fitness applications, data from devices 310 is collected and monitored to provide the user with alerts or other notifications when the user is not meeting health or fitness goals. For example, if the heart rate monitor 310(b) has detected an elevated or unhealthy heart rate, the context sensing engine 202 can combine that data with the pedometer 310(e) to determine if the user is sitting or running. In either event, behavioral nudging engine 203 may provide a vibration alert to the wrist worn device 310(c).

For grocery/health ID applications, the user may be nudged to not buy food products that do not fit with the user's health/weight goals. For instance, RFID from a wrist worn device 310(c) (e.g., with measurement happening when the user is holding the product for purchase) or object/product detection by a head worn device 310(a) may be received at context sensing engine 202. In response, context sensing engine 202 uses this information combined with behavioral goals regarding losing weight, resulting in behavioral nudging engine 203 transmitting nudges on a variety of different channels that would instruct the user put the product back because the product does not fit within specified weight loss goals.

For product compatibility applications, behavioral nudging mechanism 110 may be used to assist users determine if a product (e.g., a computer peripheral) is compatible with an existing system by combining profile information on products the user currently owns and cross referencing real time with new peripherals the user picks up off of shelf for consideration (e.g., via RFID or visual object identification/recognition).

For car and safety applications, behavioral nudging mechanism 110 recognizes kinds of behaviors correlated with past accidents in given time, place, situation (e.g., foggy, rainy) and driver characteristics. Hence, behavioral nudging mechanism 110 may provide me a nudge toward the best driving behaviors, such as staying alert and focusing on the road. The sensing can be in this case embedded in the car (e.g., GPS, control area network (CAN) bus) and also from the cloud.

Figure 5:
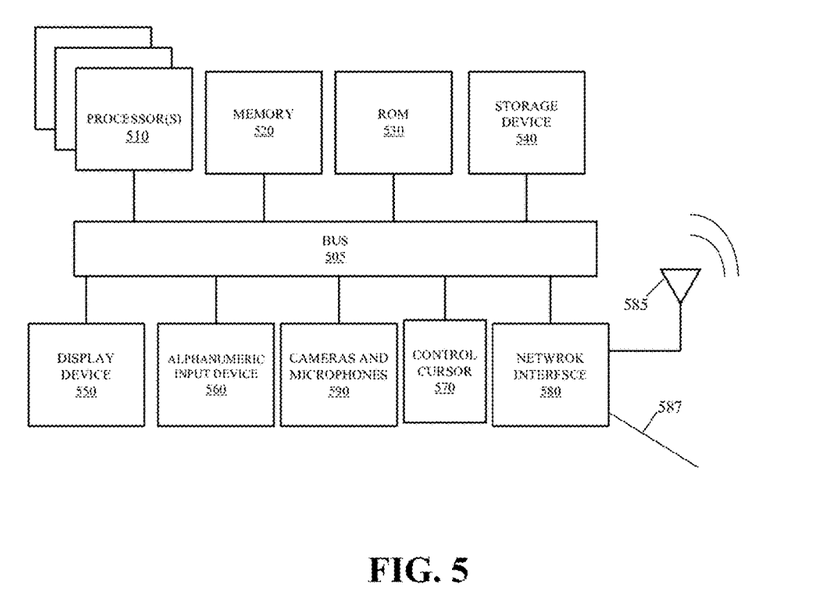
FIG. 5 illustrates a computer system suitable for implementing embodiments of the present disclosure.

FIG. 5 illustrates a computer system suitable for implementing embodiments of the present disclosure. Computing system 500 includes bus 505 (or, for example, a link, an interconnect, or another type of communication device or interface to communicate information) and processor 510 coupled to bus 505 that may process information. While computing system 500 is illustrated with a single processor, electronic system 500 and may include multiple processors and/or co-processors, such as one or more of central processors, graphics processors, and physics processors, etc. Computing system 500 may further include random access memory (RAM) or other dynamic storage device 520 (referred to as main memory), coupled to bus 505 and may store information and instructions that may be executed by processor 510. Main memory 520 may also be used to store temporary variables or other intermediate information during execution of instructions by processor 510.

Computing system 500 may also include read only memory (ROM) and/or other storage device 530 coupled to bus 505 that may store static information and instructions for processor 510. Date storage device 540 may be coupled to bus 505 to store information and instructions. Date storage device 540, such as magnetic disk or optical disc and corresponding drive may be coupled to computing system 500.

Computing system 500 may also be coupled via bus 505 to display device 550, such as a cathode ray tube (CRT), liquid crystal display (LCD) or Organic Light Emitting Diode (OLED) array, to display information to a user. User input device 560, including alphanumeric and other keys, may be coupled to bus 505 to communicate information and command selections to processor 510. Another type of user input device 560 is cursor control 570, such as a mouse, a trackball, a touchscreen, a touchpad, or cursor direction keys to communicate direction information and command selections to processor 510 and to control cursor movement on display 550. Camera and microphone arrays 590 of computer system 500 may be coupled to bus 505 to observe gestures, record audio and video and to receive and transmit visual and audio commands.

Computing system 500 may further include network interface(s) 580 to provide access to a network, such as a local area network (LAN), a wide area network (WAN), a metropolitan area network (MAN), a personal area network (PAN), Bluetooth, a cloud network, a mobile network (e.g., $3^{rd}$ Generation (3G), etc.), an intranet, the Internet, etc. Network interface(s) 580 may include, for example, a wireless network interface having antenna 585, which may represent one or more antenna(e). Network interface(s) 580 may also include, for example, a wired network interface to communicate with remote devices via network cable 587, which may be, for example, an Ethernet cable, a coaxial cable, a fiber optic cable, a serial cable, or a parallel cable.

Network interface(s) 580 may provide access to a LAN, for example, by conforming to IEEE 802.11b and/or IEEE 802.11g standards, and/or the wireless network interface may provide access to a personal area network, for example, by conforming to Bluetooth standards. Other wireless network interfaces and/or protocols, including previous and subsequent versions of the standards, may also be supported.

In addition to, or instead of, communication via the wireless LAN standards, network interface(s) 580 may provide wireless communication using, for example, Time Division, Multiple Access (TDMA) protocols, Global Systems for Mobile Communications (GSM) protocols, Code Division, Multiple Access (CDMA) protocols, and/or any other type of wireless communications protocols.

Network interface(s) 580 may include one or more communication interfaces, such as a modem, a network interface card, or other well-known interface devices, such as those used for coupling to the Ethernet, token ring, or other types of physical wired or wireless attachments for purposes of providing a communication link to support a LAN or a WAN, for example. In this manner, the computer system may also be coupled to a number of peripheral devices, clients, control surfaces, consoles, or servers via a conventional network infrastructure, including an Intranet or the Internet, for example.

It is to be appreciated that a lesser or more equipped system than the example described above may be preferred for certain implementations. Therefore, the configuration of computing system 500 may vary from implementation to implementation depending upon numerous factors, such as price constraints, performance requirements, technological improvements, or other circumstances. Examples of the electronic device or computer system 500 may include without limitation a mobile device, a personal digital assistant, a mobile computing device, a smartphone, a cellular telephone, a handset, a one-way pager, a two-way pager, a messaging device, a computer, a personal computer (PC), a desktop computer, a laptop computer, a notebook computer, a handheld computer, a tablet computer, a server, a server array or server farm, a web server, a network server, an Internet server, a work station, a mini-computer, a main frame computer, a supercomputer, a network appliance, a web appliance, a distributed computing system, multiprocessor systems, processor-based systems, consumer electronics, programmable consumer electronics, television, digital television, set top box, wireless access point, base station, subscriber station, mobile subscriber center, radio network controller, router, hub, gateway, bridge, switch, machine, or combinations thereof.

Embodiments may be implemented as any or a combination of: one or more microchips or integrated circuits interconnected using a parent board, hardwired logic, software stored by a memory device and executed by a microprocessor, firmware, an application specific integrated circuit (ASIC), and/or a field programmable gate array (FPGA). The term "logic" may include, by way of example, software or hardware and/or combinations of software and hardware.

Embodiments may be provided, for example, as a computer program product which may include one or more machine-readable media having stored thereon machine-executable instructions that, when executed by one or more machines such as a computer, network of computers, or other electronic devices, may result in the one or more machines carrying out operations in accordance with embodiments described herein. A machine-readable medium may include, but is not limited to, floppy diskettes, optical disks, CD-ROMs (Compact Disc-Read Only Memories), and magneto-optical disks, ROMs, RAMs, EPROMs (Erasable Programmable Read Only Memories), EEPROMs (Electrically Erasable Programmable Read Only Memories), magnetic or optical cards, flash memory, or other type of media/machine-readable medium suitable for storing machine-executable instructions.

Moreover, embodiments may be downloaded as a computer program product, wherein the program may be transferred from a remote computer (e.g., a server) to a requesting computer (e.g., a client) by way of one or more data signals embodied in and/or modulated by a carrier wave or other propagation medium via a communication link (e.g., a modem and/or network connection).

References to "one embodiment", "an embodiment", "example embodiment", "various embodiments", etc., indicate that the embodiment(s) so described may include particular features, structures, or characteristics, but not every embodiment necessarily includes the particular features, structures, or characteristics. Further, some embodiments may have some, all, or none of the features described for other embodiments.

In the following description and claims, the term "coupled" along with its derivatives, may be used. "Coupled" is used to indicate that two or more elements co-operate or interact with each other, but they may or may not have intervening physical or electrical components between them.

As used in the claims, unless otherwise specified the use of the ordinal adjectives "first", "second", "third", etc., to describe a common element, merely indicate that different instances of like elements are being referred to, and are not intended to imply that the elements so described must be in a given sequence, either temporally, spatially, in ranking, or in any other manner.

The following clauses and/or examples pertain to further embodiments or examples. Specifics in the examples may be used anywhere in one or more embodiments. The various features of the different embodiments or examples may be variously combined with some features included and others excluded to suit a variety of different applications. Examples may include subject matter such as a method, means for performing acts of the method, at least one machine-readable medium including instructions that, when performed by a machine cause the machine to performs acts of the method, or of an apparatus or system for facilitating hybrid communication according to embodiments and examples described herein.

Some embodiments pertain to Example 1 that includes an apparatus to facilitate behavioral nudging including one or more wearable devices having an array of sensors, a preferences and policies module to manage behavioral preferences and policies implemented to reinforce user behavior, a context sensing engine to receive data from the sensory array to determine context and use the context to determine a stimulus to nudge the user to reinforce user behavior based on stored preferences and policies; and a behavioral nudging engine to transmit the nudging stimulus to a wearable device to provide a notification to the user.

Example 2 includes the subject matter of Example 1, wherein the behavioral nudging engine is to transmit a second nudging stimulus to a second wearable device to provide a notification to the user.

Example 3 includes the subject matter of Example 1, wherein responsive to receiving context data from a first wearable device, the behavioral nudging engine is to provide a second nudging stimulus to the user via a second wearable device.

Example 4 includes the subject matter of Example 3, wherein the preferences and policies module is to keep track of user responses to the nudging stimulus.

Example 5 includes the subject matter of Example 4, wherein the preferences and policies module is to track user behavior after transmission of the nudging stimulus and to determine whether the nudging stimulus was recognized and advise corresponding to the nudging stimulus followed by the user.

Example 6 includes the subject matter of Example 4, wherein the preferences and policies perform a collaborative filtering process to determine the nudging stimulus.

Example 7 includes the subject matter of Example 8, wherein the collaborative filtering process occurs dynamically.

Example 8 includes the subject matter of Examples 1-7, further comprising a communication module and a nudging recommendation agent to communicate with two or more user devices to track user behavior and user response to nudging stimuli among the two or more user devices.

Example 9 includes the subject matter of Example 8, wherein the nudging recommendation agent observes schedule and contextual factors to reinforce behavior for each of the two or more users.

Example 10 includes the subject matter of Example 9, wherein the nudging recommendation agent observes society wide recommendations to reinforce behavior for each of the two or more users.

Example 11 includes the subject matter of Example 9, wherein the nudging recommendation agent communicates with behavioral preferences and policies module to apply acquired behavior reinforcement policies to the user.

Example 12 includes the subject matter of Examples 9-11, further comprising a user interface to enable user interaction in response to receive the nudging stimulus.

Some embodiments pertain to Example 13 that includes a method to facilitate behavioral nudging comprising receiving sensory data from one or more wearable devices, determining a context for a user wearing the one or more wearable devices based on the sensory data, determining a stimulus to nudge the user to reinforce user behavior based on stored preferences and policies and transmitting the nudging stimulus to at least one of the wearable devices via the determined mechanism to provide a notification to the user.

Example 14 includes the subject matter of Example 13, wherein the sensory data is received from a first wearable device and the nudging stimulus is provided to the user via a second wearable device.

Example 15 includes the subject matter of Example 13, further comprising tracking user responses to the nudging stimulus.

Example 16 includes the subject matter of Example 15, further comprising tracking user behavior after transmission of the nudging stimulus to determine whether the nudging stimulus was recognized and followed by the user.

Example 17 includes the subject matter of Examples 13-16, further comprising monitoring user behavior and response to nudging stimuli among two or more users.

Example 18 includes the subject matter of Examples 13-16, further comprising observing schedule and contextual factors to reinforce behavior for each of the two or more users.

Example 19 includes the subject matter of Example 18, further comprising observing society wide recommendations to reinforce behavior for each of the two or more users.

Example 20 includes the subject matter of Examples 13, further comprising detecting a response to the nudging stimulus via a user interface.

Example 21 includes the subject matter of Example 13, wherein the user interface detects a user gesture in response to the nudging stimulus.

Some embodiments pertain to Example 22 that includes at least one machine-readable medium comprising a plurality of instructions that in response to being executed on a computing device, causes the computing device to carry out operations of method claims 13-21.

Some embodiments pertain to Example 23 that includes a system to facilitate behavioral nudging comprising a first wearable device, a network coupled to the first wearable device, a second wearable device coupled to the network and a behavioral nudging unit, coupled to the network comprising a behavioral preferences and policies module to store behavioral preferences and policies implemented to reinforce user behavior, a context sensing engine to receive sensory data from the first and second wearable devices to determine context and use the context to determine a stimulus to nudge the user to reinforce user behavior based on stored preferences and policies and a behavioral nudging engine to transmit the nudging stimulus to the first wearable device to provide a notification to the user.

Example 24 includes the subject matter of Example 23, wherein the behavioral nudging engine to transmit a second nudging stimulus to the second wearable device to provide a notification to the user.

Example 25 includes the subject matter of Example 24, wherein responsive to receiving context data from a first wearable device, the behavioral nudging engine is to provide a second nudging stimulus to the user via the second wearable device.

Example 26 includes the subject matter of Examples 24 and 25, wherein the network is a body area network.

Some embodiments pertain to Example 27 that includes a system to facilitate behavioral nudging comprising means for receiving sensory data from one or more wearable devices, means for determining a context for a user wearing the one or more wearable devices based on the sensory data, means for determining a stimulus to nudge the user to reinforce user behavior based on stored preferences and policies and means for transmitting the nudging stimulus to at least one of the wearable devices via the determined mechanism to provide a notification to the user.

Example 28 includes the subject matter of Example 27, wherein the sensory data is received from a first wearable device and the nudging stimulus is provided to the user via a second wearable device.

Example 29 includes the subject matter of Examples 26 and 27, further comprising means for tracking user responses to the nudging stimulus.

Some embodiments pertain to Example 30 that includes at least one machine-readable medium comprising a plurality of instructions that in response to being executed on a computing device, causes the computing device to carry out operations comprising receiving sensory data from one or more wearable devices, determining a context for a user wearing the one or more wearable devices based on the sensory data, determining a stimulus to nudge the user to reinforce user behavior based on stored preferences and policies and transmitting the nudging stimulus to at least one of the wearable devices via the determined mechanism to provide a notification to the user.

Example 31 includes the subject matter of Example 30, wherein the sensory data is received from a first wearable device and the nudging stimulus is provided to the user via a second wearable device.

Example 32 includes the subject matter of Example 30, comprising a plurality of instructions that in response to being executed on a computing device, causes the computing device to further carry out operations comprising tracking user responses to the nudging stimulus.

Example 33 includes the subject matter of Example 32, comprising a plurality of instructions that in response to being executed on a computing device, causes the computing device to further carry out operations comprising tracking behavior after transmission of the nudging stimulus to determine whether the nudging stimulus was recognized and followed by the user.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions in any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

What is claimed is:

1. An apparatus to facilitate behavioral nudging comprising:
    a behavioral preferences and policies module to store behavioral preferences and policies implemented to reinforce user behavior, wherein the stored behavioral preferences and policies are provided by the user or an entity other than the user;
    a context sensing engine to receive data from a first of a plurality of wearable computing devices constructed to be worn on a body of the user to determine context and use the context to determine a mechanism to nudge the user to reinforce user behavior based on stored preferences and policies; and
    a behavioral nudging engine to transmit a nudging stimulus to a second of the plurality of wearable computing devices constructed to be worn on the body of the user via the determined mechanism to provide a notification to the user,
    wherein the preferences and policies module keeps track of user responses to the nudging stimulus, wherein the behavioral preferences and policies module is configured to determine one or more other nudging stimuli that are used to persuade one or more other users, and wherein the nudging stimulus is determined based on the one or more other nudging stimuli.

2. The apparatus of claim 1 wherein the behavioral nudging engine transmits a second nudging stimulus to a third of the plurality of wearable computing devices to provide a notification to the user.

3. The apparatus of claim 1 wherein the preferences and policies module tracks user behavior after transmission of the nudging stimulus to determine whether the nudging stimulus was recognized and followed by the user.

4. The apparatus of claim 1 further comprising a nudging recommendation agent to monitor a user behavior and response to the one or more nudging stimuli.

5. The apparatus of claim 4 wherein the nudging recommendation agent observes schedule and contextual factors to reinforce behavior for each of the users.

6. The apparatus of claim 4 wherein the nudging recommendation agent communicates with behavioral preferences and policies module to apply acquired behavior reinforcement policies to the user.

7. The apparatus of claim 1 further comprising a user interface to enable user interaction in response to receive the nudging stimulus.

8. A method to facilitate behavioral nudging comprising:
    receiving sensory data from a first of a plurality of wearable computing devices constructed to be worn on a body of a user;
    determining a context for the user wearing the plurality of wearable computing devices based on the sensory data;
    determining a mechanism to nudge the user to reinforce user behavior based on stored preferences and policies, wherein the stored preferences and policies are provided by the user or an entity other than the user;
    transmitting a nudging stimulus to a second of the plurality of wearable computing devices constructed to be worn on a body of the user via the determined mechanism to provide a notification to the user,
    wherein the stored preferences and policies keep track of user responses to the nudging stimulus; and
    determining one or more other nudging stimuli that are used to persuade one or more other users, wherein the nudging stimulus is determined based on the one or more other nudging stimuli.

9. The method of claim 8 further comprising tracking user behavior after transmission of the nudging stimulus to determine whether the nudging stimulus was recognized and followed by the user.

10. The method of claim 8 further comprising monitoring a user behavior and response to the one or more other nudging stimuli.

11. The method of claim 10 further comprising observing schedule and contextual factors to reinforce behavior for each of the users.

12. The method of claim 8 further comprising detecting a response to the nudging stimulus via a user interface.

13. The method of claim 12 wherein the user interface detects a user gesture in response to the nudging stimulus.

14. At least one non-transitory machine-readable medium comprising a plurality of instructions that in response to being executed on a computing device, causes the computing device to carry out operations comprising:
    receiving sensory data from a first of a plurality of wearable computing devices constructed to be worn on a body of a user;
    determining a context for the user wearing the plurality of wearable computing devices based on the sensory data;
    determining a mechanism to nudge the user to reinforce user behavior based on stored preferences and policies, wherein the stored preferences and policies are provided by the user or an entity other than the user; and
    transmitting a nudging stimulus to a second of the plurality of wearable computing devices constructed to be worn on the body of the user via the determined mechanism to provide a notification to the user,
    wherein the stored preferences and policies keep track of user responses to the nudging stimulus; and
    determining one or more other nudging stimuli that are used to persuade one or more other users, wherein the nudging stimulus is determined based on the one or more other nudging stimuli.

15. The non-transitory machine-readable medium of claim 14, comprising a plurality of instructions that in response to being executed on a computing device, causes the computing device to further carry out operations comprising tracking behavior after transmission of the nudging stimulus to determine whether the nudging stimulus was recognized and followed by the user.

16. A system to facilitate behavioral nudging comprising:
a first wearable computing device constructed to be worn on a body of a user; a network coupled to the first wearable computing device;
a second wearable computing device constructed to be worn on the body of the user,
coupled to the network; and
a behavioral nudging unit, coupled to the network comprising:
a behavioral preferences and policies module to store behavioral preferences and policies implemented to reinforce user behavior, wherein the stored behavioral preferences and policies are provided by the user or an entity other than the user;
a context sensing engine to receive sensory data from the first and second wearable computing devices to determine context and use the context to determine a mechanism to nudge the user to reinforce user behavior based on stored preferences and policies; and
a behavioral nudging engine to transmit a nudging stimulus to the first wearable computing device via the determined mechanism to provide a notification to the user,
wherein the preferences and policies module keeps track of user responses to the nudging stimulus, wherein the behavioral preferences and policies module is configured to determine one or more other nudging stimuli that are used to persuade one or more other users, and wherein the nudging stimulus is determined based on the one or more other nudging stimuli.

17. The system of claim 16 wherein the behavioral nudging engine transmits a second nudging stimulus to the second wearable computing device to provide a notification to the user.

18. The system of claim 16 wherein context data is received from the first wearable computing device and the nudging stimulus is provided to the user via the second wearable computing device.

19. The system of claim 16 wherein the network is a body area network.

* * * * *